United States Patent
Lawal et al.

(10) Patent No.: US 8,927,922 B2
(45) Date of Patent: Jan. 6, 2015

(54) FLUID DIAGNOSTIC DEVICES AND METHODS OF USING THE SAME

(71) Applicant: Aquionics, Inc., Erlanger, KY (US)

(72) Inventors: Oliver Lawal, Walton, KY (US); Paul Ropic, Walton, KY (US); Thomas L. Haslett, Ontario (CA)

(73) Assignee: Aquionics, Inc., Erlanger, KY (US)

( * ) Notice: Subject to any disclaimer, the term of this patent is extended or adjusted under 35 U.S.C. 154(b) by 0 days.

(21) Appl. No.: 14/078,825

(22) Filed: Nov. 13, 2013

(65) Prior Publication Data

US 2014/0346364 A1   Nov. 27, 2014

Related U.S. Application Data (60) Provisional application No. 61/825,589, filed on May 21, 2013.

(51) Int. Cl.
 *G01N 21/59* (2006.01)

(52) U.S. Cl.
 CPC ........................ *G01N 21/59* (2013.01)
 USPC ....................................... 250/252.1

(58) Field of Classification Search
 CPC ............... G01N 21/274; G01N 21/278; A61B 2017/00725
 USPC ......................... 250/252.1, 363.09
 See application file for complete search history.

(56) References Cited

U.S. PATENT DOCUMENTS

| | | | |
|---|---|---|---|
| 3,844,661 A | 10/1974 | Birkett et al. | |
| 4,703,175 A * | 10/1987 | Salour et al. | 356/45 |
| 5,272,345 A * | 12/1993 | Durham et al. | 250/373 |
| 7,462,835 B2 | 12/2008 | Glover | |
| 8,077,315 B2 | 12/2011 | Glover | |
| 2002/0066874 A1 | 6/2002 | Drescher | |
| 2009/0146062 A1 * | 6/2009 | Russell | 250/339.13 |
| 2009/0301175 A1 | 12/2009 | Battefeld et al. | |
| 2010/0206787 A1 | 8/2010 | Rozenberg et al. | |
| 2012/0038925 A1 | 2/2012 | Gahr et al. | |

FOREIGN PATENT DOCUMENTS

EP   0590487 A1   4/1994

OTHER PUBLICATIONS

Wedeco Hippo Ultraviolet Transmittance Measurement Monitor by Xylem; Water Online; p. 1; www.wateronline.com/doc/uv-transmittance-measurement-monitor-hippo-0003; printed from web May 29, 2013.
Wedeco TUV-15 Photometer by Xylem; Water Online; p. 1; www.wateronline.com/doc/wedeco-tun-15-photometer-0004; printed from web May 29, 2013.
International Search Report and Written Opinion dated Jan. 24, 2014 pertaining to International application No. PCT/US2013/069807.

* cited by examiner

*Primary Examiner* — Mark R Gaworecki
(74) *Attorney, Agent, or Firm* — Dinsmore & Shohl, LLP (57) ABSTRACT

A diagnostic apparatus includes a measurement head, a translating calibration element, and a calibration element actuator. The measurement head includes a diagnostic light source, a light sensor, and a measurement head body. The diagnostic light source operates at a diagnostic wavelength $\lambda_D$ and the measurement head body supports the diagnostic light source and the light sensor in a spaced apart relationship across a target fluid passageway to define a diagnostic light path extending from the diagnostic light source to the light sensor. The translating calibration element is partially transparent to light at the diagnostic wavelength $\lambda_D$ and the calibration element actuator is structurally configured to move the translating calibration element into and out of the target fluid passageway. A size and geometry of the translating calibration element is such that the translating calibration element occupies a substantial entirety of the diagnostic light path when moved into the target fluid passageway.

25 Claims, 3 Drawing Sheets

FLUID DIAGNOSTIC DEVICES AND METHODS OF USING THE SAME

CROSS REFERENCE TO RELATED APPLICATIONS

This application claims the benefit of U.S. Provisional Application No. 61/825,589, filed May 21, 2013.

TECHNICAL FIELD

The present specification generally relates to apparatuses and methods for fluid diagnostic measurements, and more specifically, apparatuses and methods for diagnostic measurements of fluids.

BACKGROUND

Ultraviolet transmittance (UVT) is a measurement of the amount of light having a certain wavelength, for example 254 nanometers, that passes through a length of a fluid. UVT values are generally provided as percentages of the amount of ultraviolet (UV) light that travels across the length of a fluid. UVT is affected by the amount of light energy that is absorbed and/or redirected by constituents in the fluid and may be expressed as a percentage of the light that passes through the fluid sample and is detected by a light sensor. For reference, distilled water having little or no constituents in the water has a UVT of almost 100%, while coffee may have a very low UVT, such as between 5-10%. Monitoring UVT for certain fluids, such as wastewater, may be important in determining suitability for consumption for example. However, accurate measurements may be difficult due to rapid fluid flow and fouling of equipment. Accordingly, alternative fluid diagnostic devices and methods may be desired.

SUMMARY

In one embodiment, a diagnostic apparatus includes a measurement head, a translating calibration element, and a calibration element actuator. The measurement head includes a diagnostic light source, a light sensor, and a measurement head body. The diagnostic light source operates at a diagnostic wavelength $\lambda_D$ and the measurement head body supports the diagnostic light source and the light sensor in a spaced apart relationship across a target fluid passageway to define a diagnostic light path extending from the diagnostic light source to the light sensor. The translating calibration element is at least partially transparent to light at the diagnostic wavelength $\lambda_D$ and the calibration element actuator is structurally configured to move the translating calibration element into and out of the target fluid passageway. A size and geometry of the translating calibration element is such that the translating calibration element occupies a substantial entirety of the diagnostic light path when moved into the target fluid passageway.

In another embodiment, a method of operating a diagnostic apparatus comprising a measurement head, a translating calibration element, and a calibration element actuator includes inserting the measurement head of the diagnostic apparatus into a target fluid such that the target fluid enters the target fluid passageway, illuminating the diagnostic light source, and measuring the amount of light emitted from the diagnostic light source that is detected by the light sensor to obtain a diagnostic reading. The method further includes calculating a target fluid value based on the diagnostic reading, moving the translating calibration element into the target fluid passageway, and measuring the amount of light emitted from the diagnostic light source that passes through the translating calibration element and is detected by the light sensor to obtain a calibration reading. The method also includes calculating a calibration value based on the calibration reading, and adjusting the target fluid value based on the calibration value.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, in which:

DETAILED DESCRIPTION

Figure 1:
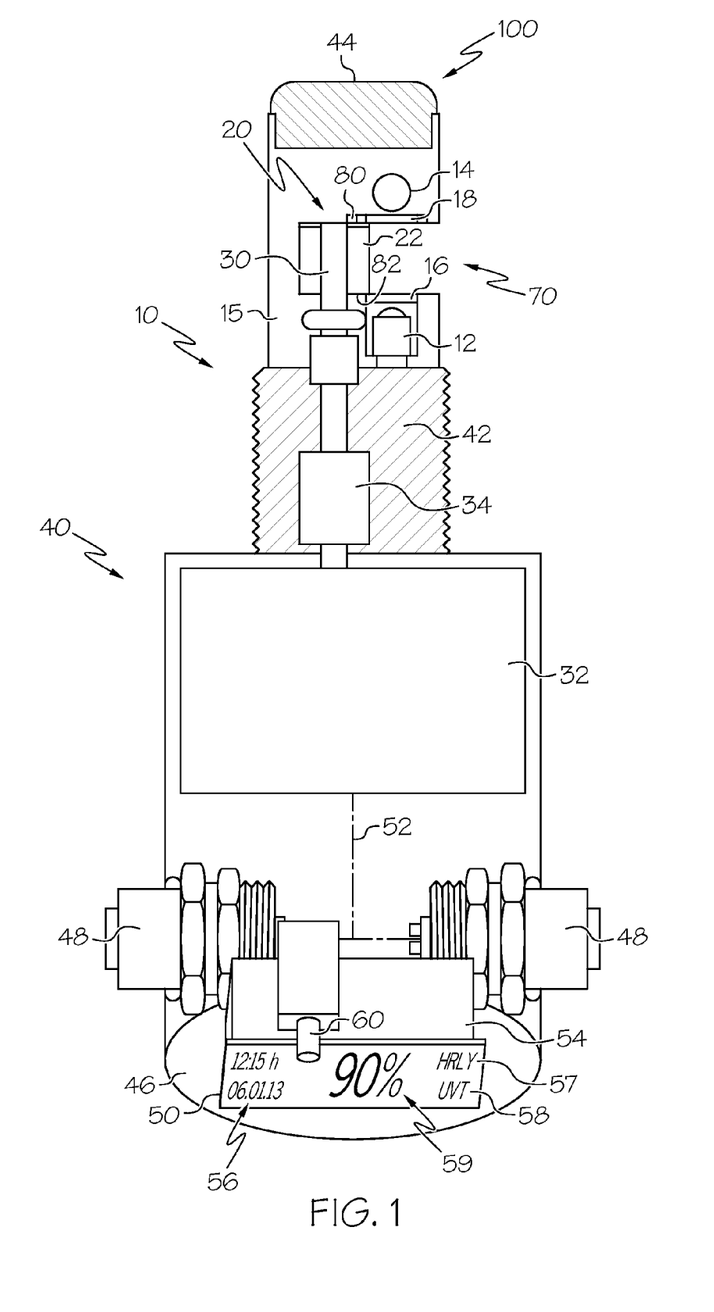
FIG. 1 depicts a front view of a fluid diagnostic device according to one or more embodiments shown and described herein.

Referring generally to FIG. 1, embodiments described herein are directed towards fluid diagnostic devices and methods, such as fluid ultraviolet transmittance (UVT) monitoring devices and methods. Particular embodiments discussed herein are directed towards water, but other fluids, including chemicals, pharmaceutical fluids, beverages, and other fluids may also be considered. The diagnostic devices described herein may be used in open or closed water methods, and for either continuous on-line measurement of a process train, or off-line samples of any type of fluid, including wastewater and drinking water. Diagnostic devices discussed herein may include measurement heads with light sources and light sensors, as well as translating calibration elements. The measurement head may be positioned in a target fluid to measure diagnostic qualities of the target fluid, such as the UVT value of the target fluid. The target fluid may flow through or otherwise enter a target fluid passageway in between the light source and the light sensor of the measurement head. The light source may be activated and the light sensor may be operable to detect a percentage of light emitted from the light source that travels through the target fluid in the target fluid passageway and is detected by the light sensor in order to obtain a target fluid value. The diagnostic device may store, display, and/or transmit the percentage of light detected by the light sensor as a target fluid value.

The translating calibration element may be actuated by a calibration element actuator, positioning the translating calibration element such that a substantial entirety of the translating calibration element is positioned between the light source and the light sensor. The translating calibration element may have a predetermined and/or known diagnostic value, such as a predetermined UVT value. The light sensor may detect the amount of light emitted from the light sensor that passes through the translating calibration element and the diagnostic device may store, display, and/or transmit the value as a calibration value. In some embodiments, the diagnostic device may compare the calibration value to a known calibration value, for example in a stored look-up table, and may adjust the target fluid value based on the calibration value. The translating calibration element may also include wipers that contact both a light sensor window positioned proximate to the light sensor and a light source window positioned proximate to the light source to remove any contaminant buildup on the light source window and the light sensor window and reduce fouling that may affect light sensor readings. In other embodiments, the wipers may contact the light source and the light sensor directly instead of the light source window and the light sensor window.

Figure 2:
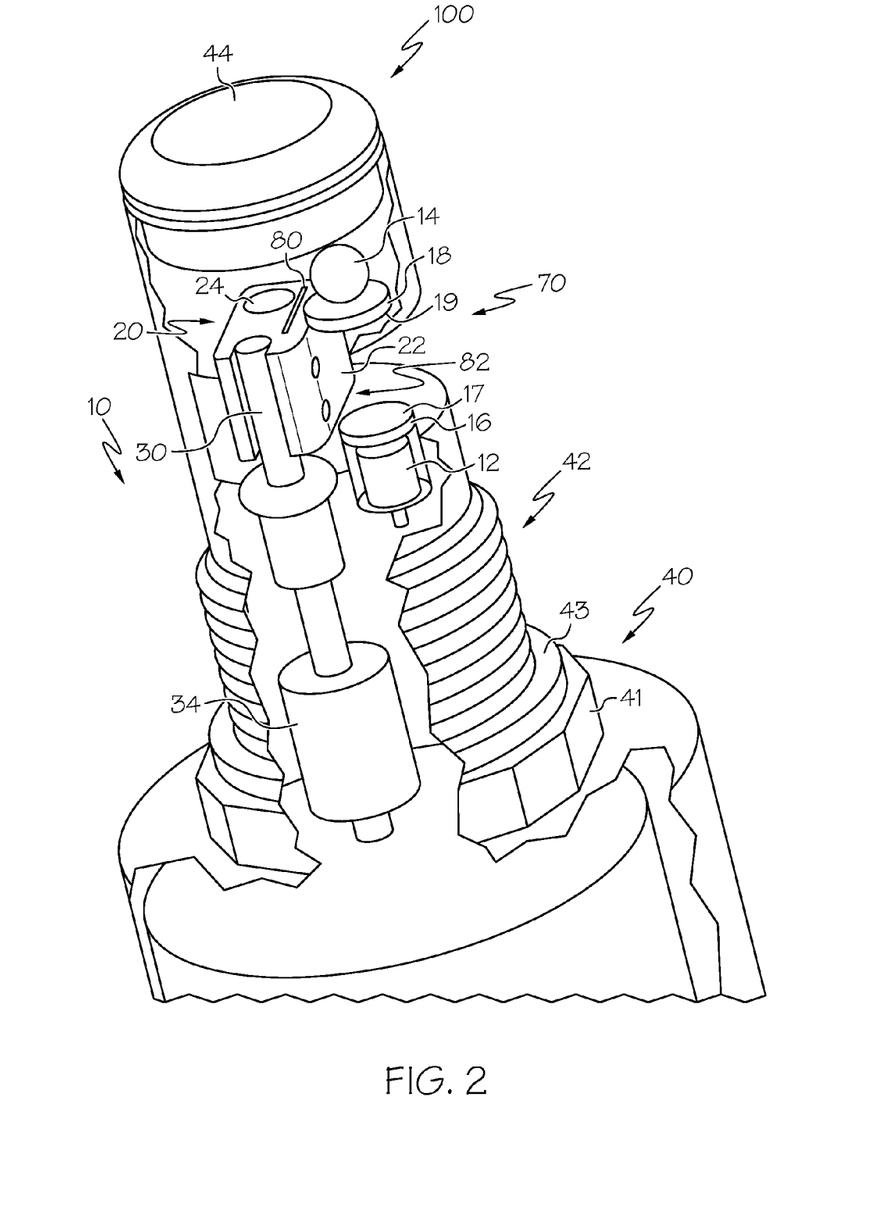
FIG. 2 depicts a close-up view of a measurement head of the fluid diagnostic device of FIG. 1 according to one or more embodiments shown and described herein.

Referring now to FIGS. 1 and 2, one embodiment of a fluid diagnostic device 100 is shown. In the illustrated embodiment, the fluid diagnostic device 100 includes a measurement head 10, a translating calibration element 20, and a calibration element actuator 30. The fluid diagnostic device 100 further includes a body portion 40 and a display 50. The measurement head 10 includes a light source 12 and a light sensor 14. The light source 12 may be for example a light emitting diode (LED), an organic LED, a liquid crystal display, or another light source, and may be operable at a diagnostic wavelength $\lambda_D$. For example, the diagnostic wavelength $\lambda_D$ may be between equal to or between approximately 180 nanometers and approximately 300 nanometers, such as 254 nanometers. The light source 12 may further comprise a ball lens package that may reduce light beam divergence. A second short focusing lens (not shown) may also be attached to the light source 12 to allow focusing on a small light sensor area. Ball lenses may also reduce sensitivity to yaw or roll.

In some embodiments where the light source 12 is an LED, the light source 12 may reach full intensity within nine nanoseconds, allowing the light source 12 to be powered on and off several times within one second. This may allow the diagnostic device 100 to collect discrete measurements. In other embodiments, the light source 12 may be left illuminated to collect continuous measurements. The light source 12 may also be operable at various wavelengths and various frequencies, as discussed below. The light source 12 may also allow for different wavelengths of light to be generated and the UVT at different wavelengths to be measured, such as wavelengths of less than 200 nanometers. This may be beneficial for applications that rely on oxidation properties of UV treatment where there is a need to characterize fluid at wavelengths below 240 nanometers. The light source 12 may also include multiple light sources that each have different wavelengths, such as one light source at 240 nanometers, one light source at 254 nanometers and one light source at 280 nanometers. This may be beneficial for treatment applications that employ polychromatic light sources where there is a need to characterize the fluid across a broad wavelength range. The light sources may then be cycled in order to collect multiple UV measurements for the different wavelengths of the light sources.

The light sensor 14 may be, for example, an ultraviolet light (UV) sensor or any light sensor configured to detect the light emitted from the light source 12. For example, the light sensor 14 may be a silicon carbide palladium (SiC Pd) sensor and may have a lens, such as a ball lens, attached to the light sensor 14. The light sensor 14 may also use alternate materials to allow different wavelength ranges to be detected, such as below 240 nanometers. The light sensor 14 may be separated a fixed distance from the light source 12, creating a diagnostic fluid path between the light sensor 14 and the light source 12.

The diagnostic device 100 does not use a mercury based UV lamp as the light source 12. Because mercury based UV lamps may have relatively high operating temperatures, for example 50-120° Celsius, the difference in temperature between the mercury based UV lamp and the target fluid may result in condensation on external surfaces of the light source window 16. The high operating temperature of mercury based UV lamps may also promote fouling on external surfaces of the light source window 16, which may be caused by organic or inorganic constituents such as iron, calcium, magnesium, or other constituents in the target fluid adhering to the external surfaces of the light source window 16 due to the heat generated by the mercury based UV lamp. The low power and lower heat generation of the light source 12 may mitigate fouling and condensation issues associated with mercury based UV lamps.

The light source 12 and the light sensor 14 are supported by a measurement head body 15 and may be positioned distanced from each other in a spaced apart relationship. A target fluid passageway 70 defining a diagnostic light path is between the light source 12 and the light sensor 14. The diagnostic light path extends from the light source 12 to the light sensor 14. The length of the target fluid passageway can vary and can be between 0.1 centimeters to 5 centimeters, for example 1 centimeter. The target fluid may enter and flow through the target fluid passageway 70. In FIG. 1, the light source 12 and the light sensor 14 are positioned substantially opposite from each other with a detection face of the light sensor 14 positioned such that the detection face substantially opposes a light emitting portion of the light source 12. The target fluid passageway 70 encompasses the area between the light source 12 and the light sensor 14, as shown in FIG. 1. In other embodiments, the light source 12 and the light sensor 14 may be positioned in another relationship, such as at an angled relationship. The measurement head 10 may further include a light source window 16 positioned proximate to the light source 12 and a light sensor window 18 positioned proximate to the light sensor 14. The light source window 16 may prevent the target fluid from contacting the light source 12, and the light sensor window 18 may likewise prevent the target fluid from contacting the light sensor 14. Other embodiments may not include the light source window 16 and/or the light sensor window 18. The light source window 16 and light sensor window 18 may be comprised of, for example, fused silica and may have a thickness of about 1 mm.

The measurement head 10 further includes a translating calibration element 20. The translating calibration element 20 may be at least partially transparent to light at the diagnostic wavelength $\lambda_D$. The translating calibration element 20 may be actuated by a calibration element actuator 30, as discussed herein. The translating calibration element 20 may be, for example, a quartz or glass rod, such as a quartz or glass cylinder. A size and geometry of the translating calibration element 20 may be such that the translating calibration element 20 occupies a substantial entirety of the diagnostic light path when moved into the target fluid passageway 70. The translating calibration element 20 may have a known and/or predetermined diagnostic value, such as a known UVT. The calibration element actuator 30 may be structurally configured to move the translating calibration element 20 into and out of the target fluid passageway 70 and may actuate the translating calibration element 20 such that the translating calibration element 20 takes up the substantial entirety of the space between the light source 12 and the light sensor 14, or the substantial entirety of the diagnostic fluid path. The calibration element actuator 30 may be any actuator configured to impart movement to the translating calibration element 20, including, for example, a manually operated mechanical coupling, such as a longitudinal rod with a finger grip, a stepper motor-driven shaft, a solenoid driven shaft, or another type of actuator. In FIG. 1, the calibration element actuator 30 is coupled to a solenoid 34. The solenoid 34 allows the calibration element actuator 30 to impart motion to the translating calibration element 20. In other embodiments, a stepper motor or manually operable device may be used to impart motion to the translating calibration element 20, as discussed herein.

The calibration element actuator 30 may move the translating calibration element 20 into and out of the target fluid passageway 70, and more specifically, into and out of the diagnostic light path. For example, the translating calibration element 20 may be rotated into and out of the diagnostic light path, or may be reciprocated or otherwise translated into and out of the diagnostic light path by the calibration element actuator 30. In the illustrated embodiment, the translating calibration element 20 is coupled to the calibration element actuator 30 by a rotating wedge 22. The rotating wedge 22 may support the translating calibration element 20 as the translating calibration element 20 is actuated by the calibration element actuator 30.

The translating calibration element 20 may allow for reference UVT measurements of the translating calibration element 20 to be collected in every instance, or as desired, in which a UVT measurement of a target fluid is collected. By taking reference UVT measurements of the translating calibration element 20 every measurement cycle, calibration drift may be minimized as regular calibration measurements may be collected. Regular reference or calibration UVT measurements may also account for light source 12 and/or light sensor 14 aging and any impact the light source 12 and or light sensor 14 age has on the UVT measurements. Further, reference UVT measurements may compensate for any incidental fouling.

In some embodiments, the diagnostic device 100 may include a second translating calibration element (not shown). The second translating calibration element may be at least partially transparent to light at the diagnostic wavelength $\lambda_D$ and have a size and geometry such that the second translating calibration element occupies a substantial entirety of the diagnostic light path when moved into the target fluid passageway 70. The second translating calibration element may have a different transparency to light at the diagnostic wavelength $\lambda_D$ than the first translating calibration element 20, which may provide the diagnostic device 100 with a second calibration reading. In yet other embodiments, the diagnostic device 100 may include multiple translating calibration elements. For example one translating calibration element may have a UVT value of 100%, a second translating calibration element may have a UVT value of 50%, a third translating calibration element may have a UVT value of 25%, and the like. Multiple translating calibration elements may allow for calibration at various UVT values.

The measurement head 10 may include a threaded portion 42, which may allow the measurement head 10 to be threadably coupled to a pipe or other vessel in which the target fluid may be resident. For example, in some embodiments, the threaded portion 42 of the measurement head 10 may be a ¾ inch standard male plug, allowing for compatibility with industry standard female openings in water or fluid transport systems. The measurement head 10 may be positioned at an inner end 44 of the diagnostic device 100 and may be inserted into the target fluid such that target fluid enters the target fluid passageway 70. Other mounting mechanisms may be included that allow the diagnostic device 100 to be inserted into or otherwise be exposed to the target fluid. For example, in applications where threaded portions are not recommended, such as beverage or pharmaceutical applications, a sanitary butt weld flange fitting may be used to couple the diagnostic device 100 to a fluid flow pipe, for example. Also, in open-top or open flow channel environments, the diagnostic device 100 may be coupled to an attachment device that includes a flexible mounting arm with a joint that allows the diagnostic device 100 to raise and lower its position relative to the fluid. For example, if the fluid level increases, the diagnostic device 100 may float to the top of the fluid in the channel due to the flexibility of the mounting arm, and therefore avoid submersion, and if the fluid level decreases, the diagnostic device may similarly change position to maintain contact between the measurement head 10 and the target fluid.

The diagnostic device 100 depicted in FIG. 1 further includes the body portion 40 and display 50. The body portion 40 may support the display 50 and may allow users to handle the diagnostic device 100 without manually contacting the measurement head 10. The body portion 40 may further include bolts 48 that allow the diagnostic device 100 to be manually rotated, for example allowing the threaded portion 42 to engage with threads in a fluid pipe. The display 50 may be positioned on an outer surface 46 of the diagnostic device 100 and may be electrically coupled to a controller 32 via connection 52. The display 50 may also be electrically coupled to a battery 54 configured to power the display 50. In other embodiments, the display 50 may be electrically coupled to an alternative power source, such as a turbine or a solar panel. In embodiments including a turbine (not shown), the turbine may be inserted into the target fluid and may generate electricity from the flow of the target fluid. In some embodiments, the controller 32 may be structurally configured to mask noise from light sensor readings by selectively removing light sensor readings attributable to wavelengths more than approximately 10% greater than or approximately 10% less than the diagnostic wavelength $\lambda_D$ as discussed herein.

The display 50 may be any one of a touchscreen display, a light emitting diode (LED) display, a liquid crystal display (LCD), an organic LED display, etc. In the embodiment shown in FIG. 1, the display 50 is an LCD display. The display 50 may be permanently backlit, allowing for ease in readability, or enabled by an operator input, for example by an external button. The display 50 may be structurally configured to display information representing the operation of the measurement head at the diagnostic apparatus. For example, the display 50 may display chronological information 56, including a date and time of a diagnostic test, as well as diagnostic information 59, such as UVT value readings. The display 50 may further display current settings, such as current diagnostic test interval time 57 and currently selected diagnostic test 58. For example, in the illustrated embodiment, the display 50 may indicate hourly diagnostic UVT tests, with a last UVT value reading of 90%. The diagnostic device 100 may also include an override button 60 which allows users to initiate an instant diagnostic test instead of waiting for a scheduled diagnostic test.

In some embodiments, the display 50 may be programmable to change color based on, for example, UVT readings. For example, if a most current UVT value reading is above about 75%, all or part of the display 50 may be programmed to glow green. Similarly, if a UVT value of between about 50% and about 75% is read, all or part of the display 50 may be programmed to glow yellow or amber. Finally, if a UVT value of below about 50% is read, all or part of the display 50 may be programmed to glow red, for example. This may allow a user or operator to quickly identify a range of the current UVT value read by the diagnostic device 100. In other embodiments, a color of the display 50 may change based on another reading or input, such as battery life or fluid flow speed for example.

In some embodiments, the diagnostic device 100 may include a communication device (not shown). The communication device may be coupled to the measurement head 10 and may be structurally configured to transmit information representing the operation of the measurement head 10 from the diagnostic device 100. For example, the communication device may transmit information via a wireless connection such as Wi-Fi, Bluetooth, text message, email, or the like. An audible alarm may also be included and may emit an alarm when a target fluid UVT or calibration reading exceeds a predetermined threshold. Results of diagnostic tests completed by the diagnostic device 100 may be transmitted as a 4-20 mA signal to the controller 32 for use as a control signal or record. Other data transmission interface protocols can be applied, such as Ethernet. Other data access methods can be applied, such as a USB port.

Referring now to FIG. 2, the measurement head 10 is depicted in detail. The measurement head 10 may be secured to the body portion 40 of the diagnostic device 100 via a nut and bolt assembly 41, for example. In some embodiments, a portion of the diagnostic device 100 may be inserted into the target fluid. For example, in some embodiments, only the measurement head 10 may be inserted through a standard pipe fitting into a water line, for example a pipe having a diameter of 3 inches, or into a side stream flow target fluid where fluid is diverted into the side stream from a mainline. In other embodiments, the entire diagnostic device 100 may be inserted into the target fluid. In yet other embodiments, the diagnostic device 100 may be a bench top device. In the embodiment illustrated in FIG. 2, the measurement head 10 of the diagnostic device 100 is inserted into the target fluid by threading the threaded portion 42 of the measurement head 10 into the target fluid vessel (not shown) containing the target fluid until rubber grommet 43 is compressed against the vessel to create an air tight seal. Other embodiments may not include the rubber grommet 43 or may include a different type of seal, such as a stainless steel washer, a plastic grommet, or the like. The target fluid may be stationary or flowing, as discussed herein.

The translating calibration element 20 may include quartz rod 24. The quartz rod 24 may be at least partially transparent to light emitted from the light source 12. Although referred to herein as a quartz cylinder, the quartz cylinder may not be a cylinder and may have a different shape, including a rectangular shape, a square shape, a prism shape, or any other shape. In addition, the quartz cylinder may be hollow to allow a measurement in air to be taken. The rod may also be constructed from an alternate material such as glass. In other embodiments, the translating calibration element 20 may not include quartz rod 24 and instead the translating calibration element 20 may itself be at least partially transparent to light emitted from the light source 12. The translating calibration element 20 may also include a wiper 80 that is structurally configured to move with the translating calibration element 20 across an optical surface of the measurement head 10 in the diagnostic light path, such as an input face 17 of the light sensor window 18. A second wiper 82 may also be included that is structurally configured to move with the translating calibration element 20 across an output face 19 of the light source window 16. The wipers 80, 82 may comprise a wiping portion and a fluid ejection portion 84 that is fluidly coupled to a fluid reservoir (not shown). The wipers 80, 82 may be structurally configured to eject fluid from the fluid ejection portion 84. The ejected fluid may contact the input face 17 and output face 19, and the wipers 80, 82 may apply pressure and/or remove the ejected fluid from the optical surfaces as the wipers 80, 82 move with the translating calibration element 20. While the wipers 80, 82 are shown in this embodiment positioned to engage optical surfaces on opposite sides of the translating calibration element 20, different configurations are possible. Further, the wipers 80, 82 may be nondestructively detachable from the translating calibration element 20.

The wipers 80, 82 may be constructed from any hard rubber, such as Viton. In the illustrated embodiment, the wipers 80, 82 may contact both the light source window 16 and the light sensor window 18 each time the quartz cylinder 24 is rotated into the diagnostic light path, clearing the windows 16, 18 of contaminants and increasing accuracy of the UV measurements. The light source 12 window and UV sensor windows may be somewhat isolated from the target fluid between measurements by the rotating wedge 22. As the rotating wedge 22 rotates, the wipers 80, 82 move across the light source and light sensor windows 16, 18, and may also move across the two ends of the quartz cylinder 24, depending on the configuration of the wipers 80, 82. The rotating wedge 22 may be removable from the diagnostic device 100, allowing the rotating wedge 22 to be replaced. This may allow for a new quartz cylinder 24 for reference measurements to be installed, along with new wipers 80, 82.

Figure 3:
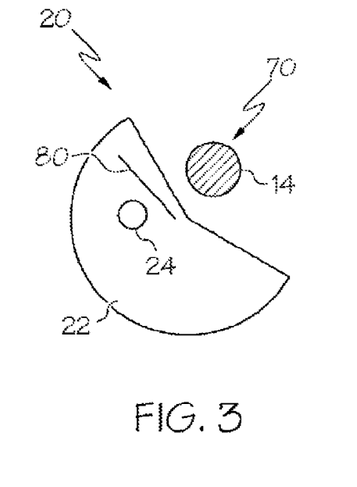
FIGS. 3-6 depict a schematic top view of the fluid diagnostic device of FIG. 1 in various positions according to one or more embodiments shown and described herein.

Referring now to FIGS. 3-6, the translating calibration element 20 is depicted in various positions. The translating calibration element 20 may allow the diagnostic device 100 to obtain a calibration value and compare the calibration value to a known value to determine a current calibration state of the diagnostic device 100. The diagnostic device 100 may adjust the target fluid value based on the calibration value, thereby increasing accuracy and allowing users to determine when the diagnostic device 100 is uncalibrated beyond a certain threshold. Referring first to FIG. 3, the translating calibration element 20 is depicted in a transmission measurement position from a top view. The light sensor 14 is shown with target fluid resident in the target fluid passageway 70. In the transmission measurement position shown in FIG. 3, the light sensor 14 detects the amount of ultraviolet light emitted from the light source 12 that passes through the target fluid to determine the UVT of the target fluid. A dark reading without the light source 12 being illuminated may provide a zero point calibration measurement for the light sensor 14.

Figure 4:
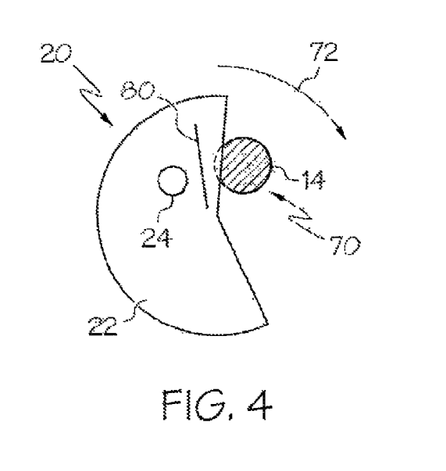
Figure 5:
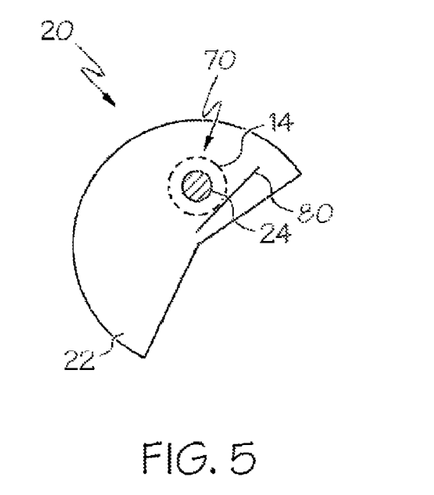

Referring now to FIG. 4, the translating calibration element 20 is depicted in a window surface cleaning position from a top view. The rotating wedge 22 rotates in direction 72. As the rotating wedge 22 rotates, the wiper 80 contacts an end face of quartz rod 24. The wiper 80 may remove contaminants and particles residing on an end face of the quartz rod 24. Referring now to FIG. 5, the translating calibration element 20 is depicted in a calibration measurement position from a top view. The quartz rod 24 is rotated into the target fluid passageway 70, and more specifically, into the diagnostic light path, allowing the diagnostic device 100 to collect a calibration measurement. The UVT of the quartz rod 24 may be known and may be compared to the measured value obtained by the diagnostic device 100. The diagnostic device 100 may adjust transmission measurements based on the calibration values.

Figure 6:
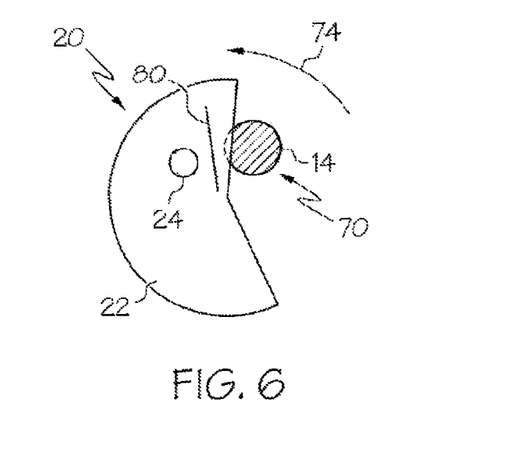

Referring now to FIG. 6, the translating calibration element 20 is depicted again in a surface cleaning position from a top view. After obtaining the calibration measurement, the translating calibration element 20 may be actuated to rotate in direction 74. The target fluid reenters the target fluid passageway 70 and the quartz rod 24 is again contacted by the wiper 80. As discussed herein, in other embodiments the wiper 80 may move with the translating calibration element 20 and may therefore contact the light source 12 and/or light sensor 14, or the respective light source window 16 and/or light sensor window 18. Some embodiments may also include additional wipers to contact both the quartz rod as well as the light source and light sensor and/or light source window and light sensor window. Additionally, if additional calibration elements are included, the additional calibration elements may be moved into the diagnostic light path and additional calibration values may be obtained for additional precision in adjustments made to target fluid values based on the calibration values.

In some embodiments, the light source 12 may be modulated at a known frequency. An electrical band pass filter may then be applied by the controller 32 to ignore all signals outside of the specific frequency band. Modulating the light source 12 may allow the diagnostic device 100 to be inserted directly into a UV reactor vessel or other area where there is a preexisting light source and to measure UVT while ignoring the effects of other light sources because of the electrical band pass filter. This may allow the diagnostic device 100 to be placed, for example, in a reactor for UV water treatment. In other embodiments, multiple light sources having different wavelengths may be included, and measurements collected by the light sensor 14 may be decoupled by modulating the light sources at different frequencies or times for targeted pathogen deactivation. Finally, because the light sources do not contain mercury, there is no concern of mercury contamination with light source 12, allowing the diagnostic device to be used in sensitive applications such as pharmaceutical manufacturing, medical devices, and the like.

One method of using the diagnostic devices discussed herein includes inserting the measurement head of the diagnostic apparatus into a target fluid such that the target fluid enters the target fluid passageway, illuminating the diagnostic light source, and measuring the amount of light emitted from the diagnostic light source that is detected by the light sensor to obtain a diagnostic reading. The method further includes calculating a target fluid value based on the diagnostic reading, moving the translating calibration element into the target fluid passageway, and measuring the amount of light emitted from the diagnostic light source that passes through the translating calibration element and is detected by the light sensor to obtain a calibration reading. The method also includes calculating a calibration value based on the calibration reading, and adjusting the target fluid value based on the calibration value. The method may also include the steps of wiping an optical surface of the measurement head with a wiping portion of a wiper structurally configured to move with the translating calibration element across the optical surface of the measurement head in the diagnostic light path, or ejecting fluid onto the optical surface of the measurement head from a fluid ejection portion of the wiper, wherein the fluid ejection portion is fluidly coupled to a fluid reservoir. In some instances, the method may include the steps of obtaining a dark reading using the measurement head while the diagnostic light source is not illuminated, comparing the dark reading to a dark value to obtain a dark calibration value, and adjusting the target fluid value based on the dark calibration value.

The above-described disclosure may allow for reduced fouling when collecting UV measurements due to low heat generation by the light source 12. Wiping the surfaces and windows periodically and reducing exposure to the target fluid may also reduce aging, fouling and calibration drift. Further, less heat is introduced to the windows in contact with the target fluid, and the light source 12 can be powered off between measurements, resulting in reduced potential for fouling and increased energy and cost savings.

Because some embodiments of the diagnostic device 100 use a light source 12 that is small in size, the diagnostic device 100 may be compact and allow the measurement head 10 of the diagnostic device 100 to be inserted directly into a pipeline with flowing water passing through the measurement head 10 of the diagnostic device 100 and then continuing along the pipeline. This allows measurements to be taken without wasting the target fluid, as the target fluid continues to flow through the pipeline. Further, real time measurements may be collected because the target fluids are tested immediately, no target fluid is diverted from the pipeline, and there is no delay between collecting the target fluid and testing the target fluid. Also, direct insertion of the diagnostic device 100 reduces the chance of the UVT properties of the target fluid from being altered by passing through a target fluid pump and/or forms of filtering. Additionally, because the light source 12 can reach full intensity within nine nanoseconds, the light source 12 can be powered on and off within short time intervals. Turning the light source 12 on and off with a known frequency may allow for dark and UVT data to be collected. This data may be used for calibration purposes and may also reduce the amount of power used and/or required to operate the diagnostic device 100. Further, the light source 12 can be powered on only for measurements and can be powered off when measurements are not required, resulting in energy and cost savings. The replacement interval for the light source 12 light source may also be increased when the light source 12 is powered on and off as opposed to leaving the light source 12 illuminated, as the light source 12 may have a fixed lifespan and usage is reduced when the light source 12 is powered off when measurements are not being collected. Reduced power consumption by powering the light source 12 on and off may allow, in some embodiments, the diagnostic device 100 to be battery powered.

The diagnostic device 100 may be an online or offline device. Online diagnostic device 100 include the elements discussed above, which are part of open or closed systems and configurable to provide continuous UV measurements for target fluids and are connected directly to the source of the target fluids. The diagnostic device 100 may also be offline, where the diagnostic device 100 are disconnected from the source of the target fluid that allow manual measurements for individual target fluids collected, for example, in a glass beaker. Offline diagnostic device 100 may be bench top devices, portable devices, or otherwise unable to provide continuous UV measurement data.

Diagnostic devices 100 disclosed herein may test and provide continuous ultraviolet transmittance measurements of target fluids. Target fluids can be of any water type or classification, including drinking water and wastewater. The target fluids discussed herein may be acquired for testing by various methods. For example, the target fluids can be acquired in a closed system, where the diagnostic device 100 is inserted directly into the main pipeline. Alternatively, a portion of water flowing through a main pipeline may be diverted into a sample pipeline that is connected to the main pipeline. The water flows through the sample pipeline, where measurements are taken as discussed herein, and back into the main pipeline, or directed to a drain. The target fluids may also be acquired in open methods, such as open-top channels with flowing water. In open methods, the diagnostic device 100 may be connected to a float to account for changes in the water level.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A diagnostic apparatus comprising a measurement head, a translating calibration element, and a calibration element actuator, wherein:
   the measurement head comprises a diagnostic light source, a light sensor, and a measurement head body;
   the diagnostic light source operates at a diagnostic wavelength $\lambda_D$;
   the measurement head body supports the diagnostic light source and the light sensor in a spaced apart relationship across a target fluid passageway to define a diagnostic light path extending from the diagnostic light source to the light sensor,
   the target fluid passageway is open on opposite sides of the diagnostic light path along the target fluid passageway;
   the translating calibration element is at least partially transparent to light at the diagnostic wavelength $\lambda_D$;
   the calibration element actuator is structurally configured to move the translating calibration element into and out of the target fluid passageway; and
   a size and geometry of the translating calibration element is such that the translating calibration element occupies a substantial entirety of the diagnostic light path when moved into the target fluid passageway.

2. The diagnostic apparatus of claim 1, wherein the diagnostic wavelength $\lambda_D$ is between approximately 180 nanometers and approximately 300 nanometers.

3. The diagnostic apparatus of claim 1, wherein the calibration element actuator comprises a solenoid, a motor, a manually operated mechanical coupling, or combinations thereof.

4. The diagnostic apparatus of claim 1, further comprising a communication device and a display, wherein:
   the communication device is coupled to the measurement head and is structurally configured to transmit information representing the operation of the measurement head from the diagnostic apparatus; and
   the display is structurally configured to display information representing the operation of the measurement head at the diagnostic apparatus.

5. The diagnostic apparatus of claim 1, further comprising a controller structurally configured to mask noise from light sensor readings by selectively removing light sensor readings attributable to wavelengths more than approximately 10% greater than or approximately 10% less than the diagnostic wavelength $\lambda_D$.

6. The diagnostic apparatus of claim 1, further comprising a power source electrically coupled to the measurement head to provide operating power to the measurement head, wherein the power source is selected from a battery, a solar panel, a turbine, or combinations thereof.

7. The diagnostic apparatus of claim 1, further comprising an additional translating calibration element, wherein:
   the additional translating calibration element is at least partially transparent to light at the diagnostic wavelength $\lambda_D$;
   a size and geometry of the additional translating calibration element is such that the additional translating calibration element occupies a substantial entirety of the diagnostic light path when moved into the target fluid passageway; and
   the translating calibration element has a different transparency to light at the diagnostic wavelength $\lambda_D$ than the additional translating calibration element.

8. The diagnostic apparatus of claim 1, wherein the calibration element actuator rotates the translating calibration element about an axis on the calibration element actuator into and out of the target fluid passageway.

9. The diagnostic apparatus of claim 1, wherein the target fluid passageway is open through at least 180° on opposite sides of the diagnostic light path along the target fluid passageway.

10. A diagnostic apparatus comprising a measurement head, a translating calibration element, and a calibration element actuator, wherein:
    the measurement head comprises a diagnostic light source, a light sensor, and a measurement head body;
    the diagnostic light source operates at a diagnostic wavelength $\lambda_D$;
    the measurement head body supports the diagnostic light source and the light sensor in a spaced apart relationship across a target fluid passageway to define a diagnostic light path extending from the diagnostic light source to the light sensor,
    the translating calibration element is at least partially transparent to light at the diagnostic wavelength $\lambda_D$;
    the calibration element actuator is structurally configured to move the translating calibration element into and out of the target fluid passageway;
    a size and geometry of the translating calibration element is such that the translating calibration element occupies a substantial entirety of the diagnostic light path when moved into the target fluid passageway; and
    a wiper that is structurally configured to move with the translating calibration element across an optical surface of the measurement head in the diagnostic light path.

11. The diagnostic apparatus of claim 10, further comprising an additional wiper, wherein the wipers are structurally configured to move with the translating calibration element across optical surfaces on opposite sides of the translating calibration element.

12. The diagnostic apparatus of claim 11, wherein:
    one of the wipers contacts an output face of the diagnostic light source; and
    another of the wipers contacts an input face of the light sensor.

13. The diagnostic apparatus of claim 10, wherein the wiper is non-destructively detachable from the translating calibration element.

14. The diagnostic apparatus of claim 10, wherein:
    the wiper comprises a wiping portion and a fluid ejection portion that is fluidly coupled to a fluid reservoir; and
    the wiper is structurally configured to eject fluid from the fluid ejection portion.

15. A method of operating a diagnostic apparatus comprising a measurement head, a translating calibration element, and a calibration element actuator, wherein:
    the measurement head comprises a diagnostic light source, a light sensor, and a measurement head body;
    the diagnostic light source operates at a diagnostic wavelength $\lambda_D$;
    the measurement head body supports the diagnostic light source and the light sensor in a spaced apart relationship across a target fluid passageway to define a diagnostic light path extending from the diagnostic light source to the light sensor;
    the target fluid passageway is open on opposite sides of the diagnostic light path along the target fluid passageway;

the translating calibration element is at least partially transparent to light at the diagnostic wavelength $\lambda_D$;

the calibration element actuator is structurally configured to move the translating calibration element into and out of the target fluid passageway;

a size and geometry of the translating calibration element is such that the translating calibration element occupies a substantial entirety of the diagnostic light path when moved into the target fluid passageway; and the method comprises:

inserting the measurement head of the diagnostic apparatus into a target fluid such that the target fluid enters the target fluid passageway;

illuminating the diagnostic light source;

measuring the amount of light emitted from the diagnostic light source that is detected by the light sensor to obtain a diagnostic reading;

calculating a target fluid value based on the diagnostic reading;

moving the translating calibration element into the target fluid passageway;

measuring the amount of light emitted from the diagnostic light source that passes through the translating calibration element and is detected by the light sensor to obtain a calibration reading;

calculating a calibration value based on the calibration reading; and     adjusting the target fluid value based on the calibration value.

16. The method of claim 15, further comprising:

obtaining a dark reading using the measurement head while the diagnostic light source is not illuminated;

comparing the dark reading to a dark value to obtain a dark calibration value; and adjusting the target fluid value based on the dark calibration value.

17. The method of claim 15, further comprising:

moving an additional translating calibration element into the target fluid passageway;

measuring the amount of light emitted from the diagnostic light source that passes through the additional translating calibration element and is detected by the light sensor to obtain an additional calibration reading;

calculating an additional calibration value based on the additional calibration reading; and adjusting the target fluid value based on the additional calibration value.

18. The method of claim 15, further comprising displaying the adjusted target fluid value on a display electrically coupled to the measurement head.

19. The method of claim 15, further comprising transmitting the adjusted target fluid value to an external computer via a communication link.

20. The method of claim 15, further comprising emitting an audible alarm when either the target fluid value or the adjusted target fluid value is greater than a predetermined threshold.

21. The method of claim 15, wherein the calibration element actuator rotates the translating calibration element about an axis on the calibration element actuator into and out of the target fluid passageway.

22. A method of operating a diagnostic apparatus comprising a measurement head, a translating calibration element, and a calibration element actuator, wherein:

the measurement head comprises a diagnostic light source, a light sensor, and a measurement head body;

the diagnostic light source operates at a diagnostic wavelength $\lambda_D$;

the measurement head body supports the diagnostic light source and the light sensor in a spaced apart relationship across a target fluid passageway to define a diagnostic light path extending from the diagnostic light source to the light sensor;

the translating calibration element is at least partially transparent to light at the diagnostic wavelength $\lambda_D$;

the calibration element actuator is structurally configured to move the translating calibration element into and out of the target fluid passageway;

a size and geometry of the translating calibration element is such that the translating calibration element occupies a substantial entirety of the diagnostic light path when moved into the target fluid passageway; and the method comprises:

inserting the measurement head of the diagnostic apparatus into a target fluid such that the target fluid enters the target fluid passageway;

illuminating the diagnostic light source;

measuring the amount of light emitted from the diagnostic light source that is detected by the light sensor to obtain a diagnostic reading;

calculating a target fluid value based on the diagnostic reading;

moving the translating calibration element into the target fluid passageway;

measuring the amount of light emitted from the diagnostic light source that passes through the translating calibration element and is detected by the light sensor to obtain a calibration reading;

calculating a calibration value based on the calibration reading; and adjusting the target fluid value based on the calibration value; and     wiping an optical surface of the measurement head with a wiping portion of a wiper structurally configured to move with the translating calibration element across the optical surface of the measurement head in the diagnostic light path.

23. The method of claim 22, further comprising ejecting fluid onto the optical surface of the measurement head from a fluid ejection portion of the wiper, wherein the fluid ejection portion is fluidly coupled to a fluid reservoir.

24. A diagnostic apparatus comprising a measurement head, a translating calibration element, and a calibration element actuator, wherein:

the measurement head comprises a diagnostic light source, a light sensor, and a measurement head body;

the diagnostic light source operates at a diagnostic wavelength $\lambda_D$;

the measurement head body supports the diagnostic light source and the light sensor in a spaced apart relationship across a target fluid passageway to define a diagnostic light path extending from the diagnostic light source to the light sensor, the translating calibration element is at least partially transparent to light at the diagnostic wavelength $\lambda_D$;

the calibration element actuator is structurally configured to move the translating calibration element into and out of the target fluid passageway by rotating the translating calibration element about a calibration element actuator axis into and out of the target fluid passageway; and a size and geometry of the translating calibration element is such that the translating calibration element occupies a substantial entirety of the diagnostic light path when moved into the target fluid passageway.

25. A method of operating a diagnostic apparatus comprising a measurement head, a translating calibration element, and a calibration element actuator, wherein:

the measurement head comprises a diagnostic light source, a light sensor, and a measurement head body;

the diagnostic light source operates at a diagnostic wavelength $\lambda_D$;

the measurement head body supports the diagnostic light source and the light sensor in a spaced apart relationship across a target fluid passageway to define a diagnostic light path extending from the diagnostic light source to the light sensor;

the translating calibration element is at least partially transparent to light at the diagnostic wavelength $\lambda_D$;

the calibration element actuator is structurally configured to move the translating calibration element into and out of the target fluid passageway by rotating the translating calibration element about an axis on the calibration element actuator into and out of the target fluid passageway;

a size and geometry of the translating calibration element is such that the translating calibration element occupies a substantial entirety of the diagnostic light path when moved into the target fluid passageway; and the method comprises:

inserting the measurement head of the diagnostic apparatus into a target fluid such that the target fluid enters the target fluid passageway;

illuminating the diagnostic light source;

measuring the amount of light emitted from the diagnostic light source that is detected by the light sensor to obtain a diagnostic reading;

calculating a target fluid value based on the diagnostic reading;

pivoting the translating calibration element into the target fluid passageway;

measuring the amount of light emitted from the diagnostic light source that passes through the translating calibration element and is detected by the light sensor to obtain a calibration reading;

calculating a calibration value based on the calibration reading;

adjusting the target fluid value based on the calibration value.

\* \* \* \* \*